United States Patent
Mazuka et al.

(10) Patent No.: US 8,697,409 B2
(45) Date of Patent: Apr. 15, 2014

(54) KETOREDUCTASE MUTANT

(75) Inventors: Fusuke Mazuka, Odawara (JP);
Takayoshi Fukushima, Odawara (JP);
Naomi Sumida, Odawara (JP); Koji Yanai, Odawara (JP)

(73) Assignee: Meiji Seika Pharma Co., Ltd., Tokyo (JP)

( * ) Notice: Subject to any disclaimer, the term of this patent is extended or adjusted under 35 U.S.C. 154(b) by 0 days.

(21) Appl. No.: 13/699,206

(22) PCT Filed: May 21, 2010

(86) PCT No.: PCT/JP2010/058631
§ 371 (c)(1),
(2), (4) Date: Nov. 20, 2012

(87) PCT Pub. No.: WO2011/145211
PCT Pub. Date: Nov. 24, 2011

(65) Prior Publication Data
US 2013/0116416 A1    May 9, 2013

(51) Int. Cl.
*C12P 19/56* (2006.01)

(52) U.S. Cl.
USPC ........................ 435/189; 435/252.3; 435/64

(58) Field of Classification Search
USPC ....................................... 435/189, 252.3, 64
See application file for complete search history.

(56) References Cited

U.S. PATENT DOCUMENTS

| | | | |
|---|---|---|---|
| 8,383,392 B2 * | 2/2013 | Sumida et al. ............. | 435/254.1 |
| 2006/0195947 A1 | 8/2006 | Davis et al. | |
| 2010/0255543 A1 | 10/2010 | Sumida et al. | |

FOREIGN PATENT DOCUMENTS

| | | | | |
|---|---|---|---|---|
| JP | 2007-502124 A | 2/2007 | | |
| WO | 2006/111561 A1 | 10/2006 | | |
| WO | 2009/035107 A1 | 3/2009 | | |
| WO | WO 2009/035107 A1 * | 3/2009 | ............... | C12N 1/21 |

OTHER PUBLICATIONS

Ke Shang, et al., "Production of 4'-epidaunorubicin by metabolic engineering of *Streptomyces coeruleorubidus* strain SIPI-1482", World J Microbiol. Biotechnol., 2008, pp. 1107-1113, vol. 24, No. 7.
Krishnamurthy Madduri, et al., "Production of the antitumor drug epirubicin (4'-epidoxorubicin) and its precursor by a genetically engineered strain of *Streptomyces peucetius*", Nat. Biotechnol., Jan. 1998, pp. 69-74, vol. 16, No. 1.
David J. Lipman, et al., "Rapid and Sensitive Protein Similarity Searches", Science, Mar. 22, 1985, pp. 1435-1441, vol. 227.
William R. Pearson, et al., "Improved tools for biological sequence comparison", Proc. Natl. Acad. Sci. USA, Apr. 1988, pp. 2444-2448, vol. 85.
Thomas Schmitt-John, et al., "Promoter constructions for efficient secretion expression in *Streptomyces lividans*", Appl. Microbiol. Biotechnol., 1992, pp. 493-498, vol. 36.
Mervyn J. Bibb, et al., "the mRNA for the 23S rRNA methylase encoded by the ermE gene of *Saccharopolyspora erythraea* is translated in the absence of a conventional ribosome-binding site", Molecular Microbiology, 1994, pp. 533-545, vol. 14, No. 3.
"Practical *Streptomyces* Genetics", Chapter 14: Gene disruption and gene replacement, The John Innes Foundation, 2000, pp. 311-338.
Mervyn J. Bibb, et al., "Cloning and analysis of the promoter region of the erthromycin resistance gene (ermE) of *Streptomyces erythraeus*", Gene 1405, 1985, pp. 215-226, vol. 38.
T. Komiyama, et al., "Baumycins, New Antitumor Antibiotics Related to Daunomycin", The Journal of Antibiotics, 1977, pp. 619-621, vol. 30, No. 7.
Natalie Lomovskaya et al., "Doxorubicin Overproduction in *Streptomyces peucetius*: Cloning and Characterization of the dnrU Ketoreductase and dnrV Genes and the doxA Cytochrome P-450 Hydroxylase Gene", Journal of Bacteriology, 1999, 181(1):305-318.

* cited by examiner

*Primary Examiner* — Tekchand Saidha
*Assistant Examiner* — Rama P Ramanujam
(74) *Attorney, Agent, or Firm* — Sughrue Mion, PLLC

(57) ABSTRACT

Disclosed are a ketoreductase mutant which can be used for an efficient production of daunorubicin derivatives, a DNA encoding the mutant, a transformant prepared by introducing the DNA thereinto to produce a daunorubicin derivative, and a process of producing a daunorubicin derivative using the transformant. The ketoreductase mutant has an amino acid sequence in which one amino acid residue or two or more amino acid residues selected from the group consisting of amino acids located at positions corresponding to the 42nd, 149th, 153rd, 270th, and 306th amino acids in the amino acid sequence of a ketoreductase (EvaE) from a chlororemomycin-producing bacterium (*Amycolatopsis orientalis*) are substituted with another amino acid residues.

10 Claims, No Drawings

SEQUENCE LISTING

<160> NUMBER OF SEQ ID NOS: 24

<210> SEQ ID NO 1
<211> LENGTH: 325
<212> TYPE: PRT
<213> ORGANISM: Amycolatopsis orientalis

<400> SEQUENCE: 1

Met Lys Leu Ile Thr Val Leu Gly Ala Ser Gly Phe Ile Gly Ser Ala
1               5                   10                  15

Val Thr Arg Ala Leu Ala Gln Gln Pro Ile Arg Leu Arg Ala Val Ala
            20                  25                  30

Arg Arg Gln Phe Thr Pro Ala Pro Gly Gln Ala Glu Thr Thr Val Val
        35                  40                  45

Ala Ala Asp Leu Thr Asp Arg Val Ala Leu Ala Asp Ala Val Ala Gly
    50                  55                  60

Ser Asp Ala Val Val Tyr Leu Leu Leu Ser Asp Gly Gly Trp Arg Ala
65                  70                  75                  80

Val Glu Thr Glu Asp Ala Glu Arg Val Asn Val Gly Val Met Arg Asp
                85                  90                  95

Leu Ile Asp Val Thr Gly Ser Asp Asn Gly Thr Pro Val Val Val
            100                 105                 110

Phe Gly Gly Thr Val Ser Gln Val Gly Val Pro Pro Arg Glu Pro Leu
        115                 120                 125

Asp Gly Ser Glu Pro Asp Asn Pro Ala Thr Pro Tyr Asp Ile Gln Lys
    130                 135                 140

Leu Thr Ala Glu Gln Ile Leu Lys Lys Ala Thr Ala Asn Gly Gln Val
145                 150                 155                 160

Arg Gly Ile Ser Leu Arg Leu Pro Thr Ile Phe Gly Glu Thr Thr Ala
                165                 170                 175

Gln Gly Ala Asn His Asp Arg Gly Val Val Ser Ser Met Ala Arg Arg
            180                 185                 190

Ala Leu Asp Gly Gln Ala Leu Thr Ile Trp Gly Asp Gly Ser Val Arg
        195                 200                 205

Arg Asp Val Val His Val Glu Asp Val Ala Ala Phe Thr Ala Ala
    210                 215                 220

Leu Ala Asn Pro Asp Ser Leu Val Gly Gly His Trp Leu Ile Gly Ala
225                 230                 235                 240

Gly Arg Gly Asp Gln Leu Gly Glu Ile Phe Arg Leu Val Ala Arg Glu
                245                 250                 255

Val Ala Glu Gln Thr Gly Gln Arg Pro Val Glu Val Thr Cys Val Glu
            260                 265                 270

Pro Pro Ser His Ala Pro Glu Met Asp Phe Arg Ser Val Thr Ile Asp
        275                 280                 285

Ser Ser Pro Phe Arg Ala Val Thr Gly Trp Arg Pro Glu Ile Ser Leu
    290                 295                 300

Ser Glu Gly Val Arg Arg Thr Val Ala Ala Leu Thr Thr Ser Val His
305                 310                 315                 320

Gly Lys Ala Arg Ala
                325

<210> SEQ ID NO 2
<211> LENGTH: 1008
<212> TYPE: DNA
<213> ORGANISM: Artificial Sequence -continued

```
<220> FEATURE:
<223> OTHER INFORMATION: Synthetic DNA

<400> SEQUENCE: 2
ggatccagcg aaggaggtgc tgagatgaag ctgatcaccg tgctcggtgc gtcgggcttc      60
atcggctcgg ctgtcacgcg tgcactggcg cagcagccaa tccggctgcg agcggtggcg     120
cgcaggcagt tcacgcccgc gcccggccaa gccgagacga ccgtcgtcgc cgctgatctc     180
accgaccgtg tcgcgctcgc cgacgcggtc gcgggatcgg acgcggtcgt gtacctgctt     240
ctgtcagacg gcggatggcg cgcggtcgag accgaggacg ccgaacgcgt gaacgtgggc     300
gtcatgcggg acctcatcga cgtcaccggc agcgacaacg ggacgccccc ggtggtggtg     360
ttcggcggta ccgtctcgca ggtcggtgtg ccacctcggg agccgctcga cggcagcgag     420
cccgacaacc cggcgactcc ctacgacata cagaagctga cagcggaaca gatcctcaag     480
aaggccacgg caaatggcca ggtgcgcggc atcagcctgc gtctgccgac gatattcggt     540
gaaaccacgg cacaaggcgc gaaccacgac cgcggtgtcg tgtcgtccat ggcgcggcga     600
gcgctcgacg gccaggcact caccatctgg ggcgacggca gcgtgcgacg cgacgtcgtc     660
catgtcgagg acgtcgcggc ggcgttcacc gcggcactgg ccaacccgga ttcccttgtc     720
ggcggccact ggctgatcgg cgcgggccga ggcgatcagc ttggggagat tttccgcctc     780
gtggcacggg aagtggccga gcagaccggg cagcgcccgg tcgaggtgac ctgtgtggaa     840
ccaccgtcgc acgcacctga gatggatttc gcagcgtca ccatcgattc ctcgccgttc      900
cgggcggtca ccggctggcg cccagagatt tcgctgtccg aaggagtgcg tcgcactgtc     960
gccgcattga cgacatcagt tcatggaaag gctcgcgcat gatctaga                 1008

<210> SEQ ID NO 3
<211> LENGTH: 18
<212> TYPE: DNA
<213> ORGANISM: Artificial Sequence
<220> FEATURE:
<223> OTHER INFORMATION: Synthetic DNA

<400> SEQUENCE: 3
gcggataaca atttcaca                                                    18

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
gtgcgggcct cttcgctatt                                                  20

<210> SEQ ID NO 5
<211> LENGTH: 39
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (19)..(19)
<223> OTHER INFORMATION: n stands for any base

<400> SEQUENCE: 5
gcggaacaga tcctcaagna cgccacggca aatggccag                             39
```

```
<210> SEQ ID NO 6
<211> LENGTH: 39
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (21)..(21)
<223> OTHER INFORMATION: n stands for any base

<400> SEQUENCE: 6
ctggccattt gccgtggcgt ncttgaggat ctgttccgc                              39

<210> SEQ ID NO 7
<211> LENGTH: 39
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (19)..(19)
<223> OTHER INFORMATION: n stands for any base

<400> SEQUENCE: 7
gcggaacaga tcctcaagnc cgccacggca aatggccag                              39

<210> SEQ ID NO 8
<211> LENGTH: 39
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (21)..(21)
<223> OTHER INFORMATION: n stands for any base

<400> SEQUENCE: 8
ctggccattt gccgtggcgg ncttgaggat ctgttccgc                              39

<210> SEQ ID NO 9
<211> LENGTH: 39
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (19)..(19)
<223> OTHER INFORMATION: n stands for any base

<400> SEQUENCE: 9
gcggaacaga tcctcaagng cgccacggca aatggccag                              39

<210> SEQ ID NO 10
<211> LENGTH: 39
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (21)..(21)
<223> OTHER INFORMATION: n stands for any base

<400> SEQUENCE: 10
ctggccattt gccgtggcgc ncttgaggat ctgttccgc                              39
```

<210> SEQ ID NO 11
<211> LENGTH: 39
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (19)..(19)
<223> OTHER INFORMATION: n stands for any base

<400> SEQUENCE: 11
gcggaacaga tcctcaagnt cgccacggca aatggccag         39

<210> SEQ ID NO 12
<211> LENGTH: 39
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (21)..(21)
<223> OTHER INFORMATION: n stands for any base

<400> SEQUENCE: 12
ctggccattt gccgtggcga ncttgaggat ctgttccgc         39

<210> SEQ ID NO 13
<211> LENGTH: 39
<212> TYPE: DNA
<213> ORGANISM: Artificial Sequence
<220> FEATURE:
<223> OTHER INFORMATION: Synthetic DNA

<400> SEQUENCE: 13
gcggaacaga tcctcaagva ggccacggca aatggccag         39

<210> SEQ ID NO 14
<211> LENGTH: 39
<212> TYPE: DNA
<213> ORGANISM: Artificial Sequence
<220> FEATURE:
<223> OTHER INFORMATION: Synthetic DNA

<400> SEQUENCE: 14
ctggccattt gccgtggcct bcttgaggat ctgttccgc         39

<210> SEQ ID NO 15
<211> LENGTH: 39
<212> TYPE: DNA
<213> ORGANISM: Artificial Sequence
<220> FEATURE:
<223> OTHER INFORMATION: Synthetic DNA

<400> SEQUENCE: 15
gcggaacaga tcctcaagtg ggccacggca aatggccag         39

<210> SEQ ID NO 16
<211> LENGTH: 39
<212> TYPE: DNA
<213> ORGANISM: Artificial Sequence
<220> FEATURE:
<223> OTHER INFORMATION: Synthetic DNA

<400> SEQUENCE: 16
ctggccattt gccgtggccc acttgaggat ctgttccgc         39

```
<210> SEQ ID NO 17
<211> LENGTH: 39
<212> TYPE: DNA
<213> ORGANISM: Artificial Sequence
<220> FEATURE:
<223> OTHER INFORMATION: Synthetic DNA

<400> SEQUENCE: 17
gcggaacaga tcctcaagat ggccacggca aatggccag                        39

<210> SEQ ID NO 18
<211> LENGTH: 39
<212> TYPE: DNA
<213> ORGANISM: Artificial Sequence
<220> FEATURE:
<223> OTHER INFORMATION: Synthetic DNA

<400> SEQUENCE: 18
ctggccattt gccgtggcca tcttgaggat ctgttccgc                        39

<210> SEQ ID NO 19
<211> LENGTH: 18
<212> TYPE: DNA
<213> ORGANISM: Artificial Sequence
<220> FEATURE:
<223> OTHER INFORMATION: Synthetic DNA

<400> SEQUENCE: 19
ttccgctgtc agcttctg                                               18

<210> SEQ ID NO 20
<211> LENGTH: 23
<212> TYPE: DNA
<213> ORGANISM: Artificial Sequence
<220> FEATURE:
<223> OTHER INFORMATION: Synthetic DNA

<400> SEQUENCE: 20
tcgatcctca agacggccac ggc                                         23

<210> SEQ ID NO 21
<211> LENGTH: 20
<212> TYPE: DNA
<213> ORGANISM: Artificial Sequence
<220> FEATURE:
<223> OTHER INFORMATION: Synthetic DNA

<400> SEQUENCE: 21
gttccacacg ggtcacctcg                                             20

<210> SEQ ID NO 22
<211> LENGTH: 20
<212> TYPE: DNA
<213> ORGANISM: Artificial Sequence
<220> FEATURE:
<223> OTHER INFORMATION: Synthetic DNA

<400> SEQUENCE: 22
cgaggtgacc cgtgtggaac                                             20

<210> SEQ ID NO 23
<211> LENGTH: 25
<212> TYPE: DNA
<213> ORGANISM: Artificial Sequence
<220> FEATURE:
<223> OTHER INFORMATION: Synthetic DNA

<400> SEQUENCE: 23
```

```
acggtcgtct cggctaggcc gggcg                                              25

<210> SEQ ID NO 24
<211> LENGTH: 25
<212> TYPE: DNA
<213> ORGANISM: Artificial Sequence
<220> FEATURE:
<223> OTHER INFORMATION: Synthetic DNA

<400> SEQUENCE: 24
gcccgcgccc ggcctagccg agacg                                              25
```

KETOREDUCTASE MUTANT

CROSS REFERENCE TO RELATED APPLICATIONS

This application is a National Stage of International Application No. PCT/JP2010/058631 filed May 21, 2010, the contents of all of which are incorporated herein by reference in their entirety.

TECHNICAL FIELD

The present invention relates to a ketoreductase mutant which can be used for a microbial fermentation process of semi-synthetically producing daunorubicin derivatives.

BACKGROUND ART

Anthracyclin antibiotics are a class of aromatic polyketides, and are pigment glycosides composed of an aglycon moiety, of which the basic skeleton is 7,8,9,10-tetrahydro-5,12-naphthacenequinone with the following chemical formula, and a sugar moiety, which is mainly composed of amino sugar(s).

[Chem. 1]

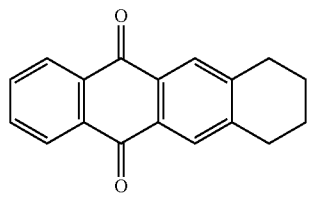

Anthracyclin antibiotics bind with DNA and generate radicals, which cleave the DNA strands or inhibit topoisomerase II. Topoisomerase has a DNase activity and a ligase activity, and catalyzes the transient cleavage of DNA strands and the religation thereof. Anthracyclin antibiotics damage DNA replication by inhibiting topoisomerase II, and exert their antitumor activity. The anthracyclin antibiotics have accumulated cardiac toxicity, but are considered to be an effective antitumor drug because of their wide spectrum of antitumor activity.

Anthracyclin antitumor drugs that are currently used include compounds, such as daunorubicin, which are derived from fermentation products, and semi-synthetic products such as doxorubicin or epirubicin, which are produced from daunorubicin as a starting material.

[Chem. 2]

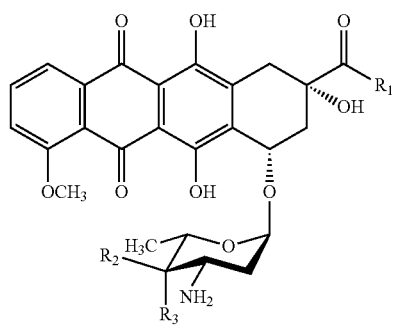

TABLE 1

| | $R_1$ | $R_2$ | $R_3$ |
|---|---|---|---|
| Daunorubicin | $CH_3$ | H | OH |
| Doxorubicin | $CH_2OH$ | H | OH |
| Epidaunorubicin | $CH_3$ | OH | H |
| Epirubicin | $CH_2OH$ | OH | H |

Epirubicin is superior to daunorubicin and doxorubicin in antitumor activity and toxicity, but has disadvantages in production cost. This is because epirubicin is produced from daunorubicin as a starting material, but the process includes a chemical synthesis step of reversing the hydroxyl group at 4-position of the amino sugar moiety with a low yield.

It was reported that a gene encoding a ketoreductase (epi-type ketoreductase), different in the stereospecificity of products from a ketoreductase involved in the biosynthesis of daunorubicin, was introduced into a daunorubicin-producing bacterium, and the biosynthesis pathway of daunorubicin was modified to produce epidaunorubicin by direct fermentation (non-patent literature 1). Epidaunorubicin has the same conformation of the hydroxyl group of the amino sugar moiety as epirubicin, and thus, epidaunorubicin can be used as an extremely useful starting material for the production of epirubicin. It was reported that when the epi-type ketoreductase gene (avrE) involved in the biosynthesis of avermectin was introduced, the transformant produced the largest amount of epidaunorubicin. However, the amount produced was only approximately 54 μg/mL, which did not reach a practically useful level.

Further, a patent application in which the epidaunorubicin-producing bacterium obtained in non-patent literature 1 was treated with a mutagen to increase the productivity of epidaunorubicin to 100 μg/mL or more was filed (patent literature 1), but the obtained mutant was not described in detail in the Examples.

The present inventors found that when a ketoreductase gene (evaE) involved in the biosynthesis of epivancosamine, which was an amino sugar contained in chlororemomycin, was introduced, the amount of epidaunorubicin produced was increased by a factor of 2.7 in comparison with the case where the avrE gene was introduced, and filed a patent application (patent literature 2).

CITATION LIST

Patent Literature

[Patent literature 1] WO 2006/111561
[Patent literature 2] WO 2009/035107

Non-Patent Literature

[Non-patent literature 1] Madduri, K. et al., Nature Biotechnology, (U.S.A.), 1998, vol. 16, p. 69-74
[Non-patent literature 2] Lipman D J and Pearson W R, Science, (U.S.A.), 1985, vol. 227, p. 1435-1441 (4)
[Non-patent literature 3] Lipman D J and Pearson W R, Proceedings of the National Academy of Sciences of the United States of America, (U.S.A.), 1988, vol. 85, p. 2444-2448
[Non-patent literature 4] Schmitt-John, T. and Engels, J. W., Applied Microbiology and Biotechnology, (Germany), 1992, vol. 36, p. 493-498
[Non-patent literature 5] Bibb, M. J. et al., Molecular Microbiology, (United Kingdom), 1994, vol. 14, p. 533-545

[Non-patent literature 6] Practical *Streptomyces* Genetics, The John Innes Foundation, (United Kingdom), Norwick, 2000, p. 311-338

[Non-patent literature 7] Bibb, M. J. et al., Gene, (United Kingdom), 1985, vol. 38, p 215-226

[Non-patent literature 8] Komiyama, T. et al., The Journal of Antibiotics, (Japan), 1977, vol. 30, p. 619-621

SUMMARY OF INVENTION

Technical Problem

With respect to a ketoreductase which can be used for a microbial direct fermentation of daunorubicin derivatives such as epidaunorubicin, an object of the present invention is to provide a ketoreductase mutant which is modified so as to improve the productivity of a daunorubicin derivative.

Solution to Problem

The present inventors conducted intensive studies on the modification of a ketoreductase (EvaE) consisting of the amino acid sequence of SEQ ID NO: 1, as a ketoreductase which can be used for a microbial direct fermentation of daunorubicin derivatives, and found that the productivity of a daunorubicin derivative was improved by using a ketoreductase mutant in which at least an amino acid selected from the group consisting of the 42nd, 149th, 153rd, 270th, and 306th amino acids in the amino acid sequence is substituted with another amino acid, and completed the present invention.

The present invention provides a ketoreductase mutant which can be used for a microbial direct fermentation process of efficiently producing daunorubicin derivatives, and a polynucleotide (particularly DNA) which encodes the mutant. The present invention provides a transformant with the DNA encoding the ketoreductase mutant of the present invention, and a process of producing a daunorubicin derivative comprising cultivating the transformant, and collecting the daunomycin derivative from the obtained culture broth. The present invention provides a daunorubicin derivative produced by the transformant of the present invention.

The present invention provides:

[1] A ketoreductase mutant which is derived from a ketoreductase enzyme which can be used for a fermentation production of a daunomycin derivative, wherein a mutation in the amino acid sequence of the parent ketoreductase is an insertion, a substitution, or a deletion of one or plural amino acids, or an addition of one or plural amino acids to one or both ends thereof, and wherein the productivity of the daunomycin derivative is improved in comparison with a case using the parent ketoreductase.

[2] The ketoreductase mutant of [1], characterized in that the parent ketoreductase comprises an amino acid sequence having a 90% or more identity with the amino acid sequence of SEQ ID NO: 1.

[3] The ketoreductase mutant of [2], wherein one amino acid residue or two or more amino acid residues selected from the group consisting of amino acids located at positions corresponding to the 42nd, 149th, 153rd, 270th, and 306th amino acids in the amino acid sequence of SEQ ID NO: 1 are substituted with another amino acid residues.

[4] The ketoreductase mutant of [3], wherein the amino acid located at the position corresponding to the 42nd amino acid in the amino acid sequence of SEQ ID NO: 1 is substituted with leucine.

[5] The ketoreductase mutant of [3], wherein the amino acid located at the position corresponding to the 149th amino acid in the amino acid sequence of SEQ ID NO: 1 is substituted with serine.

[6] The ketoreductase mutant of [3], wherein the amino acid located at the position corresponding to the 153rd amino acid in the amino acid sequence of SEQ ID NO: 1 is substituted with an amino acid other than proline.

[7] The ketoreductase mutant of [3], wherein the amino acid located at the position corresponding to the 270th amino acid in the amino acid sequence of SEQ ID NO: 1 is substituted with arginine.

[8] The ketoreductase mutant of [3], wherein the amino acid located at the position corresponding to the 306th amino acid in the amino acid sequence of SEQ ID NO: 1 is substituted with aspartic acid.

[9] The ketoreductase mutant of any one of [1] to [8], wherein the daunomycin derivative is epidaunomycin.

[10] A polynucleotide which encodes the ketoreductase mutant of any one of [1] to [9].

[11] A transformant which is prepared by introducing the polynucleotide of [10] into a host actinobacterium originally capable of producing daunomycin to impart an ability to produce a daunomycin derivative.

[12] The transformant of [11], wherein the host actinobacterium is *Streptomyces coeruleorubidus*.

[13] A process of producing a daunomycin derivative, comprising the steps of: cultivating the transformant of [12], and collecting the daunomycin derivative from the obtained culture broth.

[14] A daunomycin derivative obtainable by the process of [13].

Advantageous Effects of Invention

According to the ketoreductase mutant of the present invention, the productivity of a daunorubicin derivative can be improved.

DESCRIPTION OF EMBODIMENTS

The ketoreductase mutant of the present invention may be obtained by modifying a parent ketoreductase. The mutation in the present invention means an insertion, a substitution, or a deletion of one or plural amino acids in the amino acid sequence of the ketoreductase, or an addition of one or plural amino acids to one or both ends of the sequence, wherein the productivity of a daunomycin derivative is improved when the ketoreductase mutant is used for a fermentation of the daunorubicin derivative, in comparison with a case using the parent ketoreductase.

The parent ketoreductase used in the present invention is not limited, so long as it can be used for a fermentation of a daunorubicin derivative. A ketoreductase consisting of the amino acid sequence of SEQ ID NO: 1, or a homologous protein thereof is preferable. The term "homologous protein" as used herein means a protein in which one or several amino acids are inserted, substituted, or deleted in the amino acid sequence of SEQ ID NO: 1, or one or several amino acids are added at one or both ends of the amino acid sequence, and which has a 90% or more identity with the amino acid sequence of SEQ ID NO: 1, and maintains ketoreductase activity. The term "identity" as used herein means a value calculated by FASTA3 [fasta.ddbj.nig.ac.jp/top-j.html], [Science, 227, 1435-1441 (1985); and Proc. Natl. Acad. Sci. USA, 85, 2444-2448 (1988) (non-patent literatures 2 and 3)], a known homology search program, in accordance with default parameters. The presence or absence of the ketoreductase activity can be determined by introducing a gene encoding a homologous protein into an appropriate host as described below to express the homologous protein, and determining the presence or absence of a daunorubicin derivative generated. It is obvious for those skilled in the art to select and prepare such a homologous protein without undue experimentation, with reference to the sequence of SEQ ID NO: 1.

In a case that the parent ketoreductase consists of the amino acid sequence of SEQ ID NO: 1, a mutant in which one amino acid residue, or two or more amino acid residues selected from the group consisting of the 42nd, 149th, 153rd, 270th, and 306th amino acids in the sequence are substituted with another amino acid residues may be exemplified as a preferred embodiment of the present invention.

According to a preferred embodiment of the present invention, preferred examples of such a mutant include a mutant having a substitution of the 42nd amino acid with leucine, a mutant having a substitution of 149th amino acid with serine, a mutant having a substitution of the 153rd amino acid with an amino acid other than proline, a mutant having a substitution of the 270th amino acid with arginine, and a mutant having a substitution of the 306th amino acids with aspartic acid. These mutants exhibit advantageous properties to improve the productivity of a daunorubicin derivative, when they are used for a fermentation of the daunorubicin derivative.

In a case that the parent ketoreductase is a homologous protein derived from the amino acid sequence of SEQ ID NO: 1, a mutant in which one amino acid residue, or two or more amino acid residues selected from the group consisting of amino acids located at positions corresponding to the 42nd, 149th, 153rd, 270th, and 306th amino acids in the sequence are substituted with another amino acid residues may be exemplified. The location of the amino acid residue(s) to be substituted in a homologous protein derived from the parent ketoreductase consisting of the amino acid sequence of SEQ ID NO: 1 may be easily selected by a comparison of amino acid sequences using a known algorithm. In a case that the comparison of amino acid sequences using a known algorithm is difficult, the location of the amino acid residue(s) to be substituted may be specified by a comparison of the three-dimensional structures of enzymes.

A transformant which produces a daunorubicin derivative may be obtained by introducing a DNA encoding the ketoreductase mutant of the present invention into an appropriate host originally capable of producing daunorubicin. A preferred host is actinobacteria, and *Streptomyces peuceticus* and *Streptomyces coeruleorubidus* are known as actinobacteria capable of producing daunorubicin. These microorganisms may be used as the host into which a DNA encoding the ketoreductase mutant of the present invention is introduced. Actinobacteria capable of producing baumycin may be used as the host, because baumycin is a substance in which the amino sugar moiety (L-daunosamine) of daunorubicin is modified, and daunorubicin is an intermediate of the biosynthesis of baumycin. As these daunorubicin- or baumycin-producing microorganisms, a strain deficient in producing daunorubicin in which a ketoreductase gene involved in the biosynthesis of the hydroxyl group at 4-position of the L-daunosamine moiety of daunorubicin is deleted is preferably used.

The gene may be introduced into the host by a conventional method, for example, a method of mixing protoplasts with the desired DNA, a method utilizing a phage, or a method utilizing conjugal transfer. These methods may be appropriately selected in accordance with the properties of the host. To select strains into which the epi-type ketoreductase gene of interest is introduced, it is preferable that the gene is introduced together with a vector comprising a selective marker. The selective marker is not particularly limited, so long as strains into which the epi-type ketoreductase gene is introduced can be selected. Preferred selective markers include a kanamycin resistance gene, a streptomycin resistance gene, a hygromycin resistance gene, a viomycin resistance gene, and an apramycin resistance gene. It is preferable that a promoter sequence which functions in the host is added to the epi-type ketoreductase gene to be introduced, and examples of a preferred promoter include an ermE* promoter derived from an erythromycin resistance gene [Schmitt-John, T. and Engels, J. W., Applied Microbiology and Biotechnology, (Germany), 1992, vol. 36, p. 493-498 (non-patent literature 4); and Bibb, M. J. et al., Molecular Microbiology, (United Kingdom), 1994, vol. 14, p. 533-545 (non-patent literature 5)]. The state of the epi-type ketoreductase gene introduced into the host is not particularly limited. For example, the gene may be introduced into a plasmid which can extrachromosomally self-duplicate, or into a chromosome, or may be introduced into the host by replacing the epi-type ketoreductase gene with a ketoreductase gene of the host involved in the biosynthesis of the hydroxyl group at 4-position of the L-daunosamine moiety of daunorubicin. The replacement of the gene may be carried out utilizing a method which is conventionally used for actinobacteria [Practical *Streptomyces* Genetics, The John Innes Foundation, (United Kingdom), Norwick, 2000, p. 311-338 (non-patent literature 6)].

Daunorubicin derivatives produced by the transformant of the present invention are daunorubicin derivatives in which the hydroxyl group at 4-position of the L-daunosamine moiety of daunorubicin is reversed, preferably epidaunorubicin or epirubicin, and more preferably epidaunorubicin.

The transformant of the present invention may be cultivated in accordance with a conventional method to produce the daunorubicin derivatives, using a medium including conventional components. As carbon sources, for example, glucose, sucrose, syrup, dextrin, starch, glycerol, molasses, animal oils, or vegetable oils may be used. As nitrogen sources, soybean meal, wheat germ, corn steep liquor, cotton seed meal, meat extract, polypeptone, malt extract, yeast extract, ammonium sulfate, sodium nitrate, or urea may be used. If desired, it is preferable that inorganic salts capable of generating sodium, potassium, calcium, magnesium, cobalt, chlorine, phosphoric acid (such as dipotassium hydrogen phosphate), sulfuric acid (such as magnesium sulfate), or other ions may be supplemented. Further, if desired, thiamine (such as thiamine hydrochloride) or other vitamins; glutamic acid (such as sodium glutamate), asparagine (such as DL-asparagine), or other amino acids; nucleotides or other micronutrients; or antibiotics or other selection agents may be supplemented. Furthermore, organic or inorganic substances capable of promoting the growth of the transformant and the production of the daunorubicin derivatives may be appropriately added.

The pH of the medium is, for example, approximately 5.5 to 8. The cultivation may be carried out by a solid cultivation under aerobic conditions, a shaking cultivation, an agitating cultivation with aeration, or a submerged cultivation with aeration, and most preferably a submerged cultivation with aeration. Appropriate temperatures for cultivation are 15° C. to 40° C., and the transformant can grow at approximately 25° C. to 35° C. in almost all cases. The production of the daunorubicin derivatives varies in accordance with the medium, cultivation conditions, or the type of the host, but the accumulation of the products generally reaches its maximum after 2 to 10 days in any cultivation. When the amounts of the daunorubicin derivatives reach the maximum during the cultivation, the cultivation is stopped, and the desired products are isolated and purified from the resulting culture.

To collect the daunorubicin derivatives from the culture obtained by cultivating the transformant of the present invention, the extraction and purification thereof from the culture can be carried out using a conventional separation method, which may be selected in accordance with their properties, for example, solvent extraction, an ion exchange resin method, adsorption or partition column chromatography, gel filtration, dialysis, precipitation, or crystallization alone, or an appropriate combination thereof. The resulting daunorubicin derivatives can be further purified by chromatography using an adsorbing agent such as silica gel or alumina, Sephadex LH-20 (manufactured by Pharmacia), or TOYOPEARL HW-40 (manufactured by TOSOH Corporation).

The present invention now will be further illustrated by, but is by no means limited to, the following Examples. Various changes and modifications are possible without departing from the scope of the appended claims.

Example 1

Introduction of mutations into ketoreductase gene (evaE) from chlororemomycin-producing bacterium (*Amycolatopsis orientalis*)

Plasmid pIJ4070 [Bibb, M. J. et al., Gene, (United Kingdom), 1985, vol. 38, p 215-226 (non-patent literature 7)] comprising an ermE* promoter was double-digested with EcoRI and BamHI, and fractionated by electrophoresis, and an EcoRI-BamHI fragment of approximately 0.3 kbp comprising the ermE* promoter was extracted from the gel. This DNA fragment was inserted between the EcoRI and BamHI sites of plasmid pSET152 to obtain plasmid pSET152-E*.

With respect to a ketoreductase gene (evaE) from a chlororemomycin-producing bacterium (*Amycolatopsis orientalis*), a BamHI-XbaI fragment consisting of the nucleotide sequence of SEQ ID NO: 2, of which the full sequence was chemically synthesized, was inserted between the BamHI and XbaI sites of plasmid pSET152-E* to obtain plasmid pEVA-E. Random mutations were introduced into the evaE fragment, using plasmid pEVA-E as the template, using a GeneMorph II Random Mutagenesis Kit (manufactured by Stratagene) according to a manual attached thereto, and using a combination of primer pSET153-R (5'-GCGGATAA-CAATTTCACA-3', SEQ ID NO: 3) and primer pSETermE-R (5'-GTGCGGGCCTCTTCGCTATT-3', SEQ ID NO: 4).

The resulting evaE fragments into which mutations were introduced were double-digested with BamHI and XbaI, and cloned between the BamHI and XbaI sites of plasmid pSET152-E* to prepare a genomic DNA library.

An *Escherichia coli* strain ET12567/pUZ8002 containing this genomic DNA library was inoculated into 100 mL of an LB liquid medium (1% Difco bacto tryptone, 0.5% Difco yeast extract, 0.5% NaCl, and 0.1% glucose) containing 25 µg/mL chloramphenicol, 25 µg/mL kanamycin, and 50 µg/mL apramycin, and cultivated at 37° C. overnight to prepare a preculture. This preculture was inoculated into the same LB liquid medium to give a final concentration of 1%, and cultivated at 37° C. for about 4 hours. After the cultivation, *E. coli* was washed with the LB liquid medium twice, and finally suspended in 10 mL of the LB liquid medium to prepare a liquid of *E. coli*.

A dnmV-disrupted strain (patent literature 2: WO2009/035107) of *Streptomyces coeruleorubidus* capable of producing daunorubicin was inoculated on an MS agar medium (2% S soybean meal, 2% mannitol, and 2% agar), and cultivated at 28° C. for 4 days. After the cultivation, spores were scraped with 3 mL of a 20% glycerol solution to prepare a liquid of host spores.

After 500 µL of the liquid of host spores was mixed with 500 µL of the liquid of *E. coli*, the collected mixture was inoculated on an MS agar medium supplemented with $MgCl_2$ (final concentration: 10 mmol/L). After cultivation at 28° C. for 20 hours, 1 mL of sterile water containing 1 mg of apramycin and 1.5 mg of nalidixic acid was layered on the MS agar medium. Cultivation at 28° C. for 5 days was carried out to obtain apramycin-resistant strains.

To confirm the production of epidaunorubicin in these strains, each strain was inoculated into 10 mL of a liquid production medium [Komiyama, T. et al., The Journal of Antibiotics, (Japan), 1977, vol. 30, p. 619-621 (non-patent literature 8)] prepared in a test tube, and cultivated at 28° C. for 2 days. Further, 1 mL of each culture was inoculated into 20 mL of the same liquid production medium prepared in a 250-mL Erlenmeyer flask, and cultivated at 32° C. for 7 days while shaking. To extract products generated by each strain, 1 mL of each culture, 1 mL of methanol, and 70 µL of 50% $H_2SO_4$ were added to 15-mL centrifuge tubes, shaken for 1 hour, refrigerated overnight, and centrifuged at 2000×g for 10 minutes, and the resulting supernatants were subjected to HPLC analysis.

Genomic DNAs were prepared from the obtained clones having a high productivity using an apparatus for purification of genomic DNA (MagExtractor, manufactured by TOYOBO Co., Ltd.) in accordance with a protocol attached thereto, and a PCR was carried out using a combination of primer pSET153-R (SEQ ID NO: 3) and primer pSETermE-R (SEQ ID NO: 4), together with a PrimeSTAR HS DNA Polymerase (manufactured by Takara Bio Inc.), under the following cycle conditions (a cycle consisting of a reaction at 98° C. for 10 seconds, a reaction at 60° C. for 5 seconds, and a reaction at 72° C. for 1 minute was repeated 25 times). As a result, amplified DNA fragments of approximately 1 kbp were obtained. The resulting DNA fragments were sequenced, and it was found that those clones showing a high productivity had any one of amino acid substitutions of Q42L (the 42nd glutamine was substituted with leucine), K153T (the 153rd lysine was substituted with threonine), and C270R (the 270th cysteine was substituted with arginine).

TABLE 2

| Strain | Amount of epidaunorubicin produced (relative ratio %) |
|---|---|
| evaE | 100 |
| evaE/Q42L | 117 |
| evaE/K153T | 154 |
| evaE/C270R | 137 |

Example 2

Introduction of Saturation Mutations into Plasmid pEVA-E

A PCR was carried out, using plasmid pEVA-E constructed in Example 1 as the template, the following primer sets, and a PrimeSTAR HS DNA polymerase (manufactured by Takara Bio Inc.), by repeating a cycle consisting of a reaction at 98° C. for 10 seconds and a reaction at 68° C. for 7 minutes 25 times. The capital letters in the following primer nucleotide sequences represent portions into which saturation mutations are introduced.

[1] NAC-F
(SEQ ID NO: 5)
5'-gcggaacagatcctcaagNACgccacggcaaatggccag-3'

NAC-R
(SEQ ID NO: 6)
5'-ctggccatttgccgtggcGTNcttgaggatctgttccgc-3'

[2] NCC-F
(SEQ ID NO: 7)
5'-gcggaacagatcctcaagNCCgccacggcaaatggccag-3'

NCC-R
(SEQ ID NO: 8)
5'-ctggccatttgccgtggcGGNcttgaggatctgttccgc-3'

[3] NGC-F
(SEQ ID NO: 9)
5'-gcggaacagatcctcaagNGCgccacggcaaatggccag-3'

NGC-R
(SEQ ID NO: 10)
5'-ctggccatttgccgtggcGCNcttgaggatctgttccgc-3'

[4] NTC-F
(SEQ ID NO: 11)
5'-gcggaacagatcctcaagNTCgccacggcaaatggccag-3'

NTC-R
(SEQ ID NO: 12)
5'-ctggccatttgccgtggcGANcttgaggatctgttccgc-3'

[5] VAG-F
(SEQ ID NO: 13)
5'-gcggaacagatcctcaagVAGgccacggcaaatggccag-3'

VAG-R
(SEQ ID NO: 14)
5'-ctggccatttgccgtggcCTBcttgaggatctgttccgc-3'

[6] TGG-F
(SEQ ID NO: 15)
5'-gcggaacagatcctcaagTGGgccacggcaaatggccag-3'

TGG-R
(SEQ ID NO: 16)
5'-ctggccatttgccgtggcCCActtgaggatctgttccgc-3'

[7] ATG-F
(SEQ ID NO: 17)
5'-gcggaacagatcctcaagATGgccacggcaaatggccag-3'

ATG-R
(SEQ ID NO: 18)
5'-ctggccatttgccgtggcCATcttgaggatctgttccgc-3'

The obtained PCR products were digested with 1 µL (20 units or less) of DpnI at 37° C. for 1 hour. *Escherichia coli* DH5α (manufactured by Takara Bio Inc.) was transformed with 1 µL of each DpnI-digested product, inoculated on LB agar medium plates containing 50 µg/mL apramycin, and cultivated at 37° C. overnight.

The grown colonies were subjected to a colony PCR using an LaTaq polymerase (manufactured by Takara Bio Inc.) under the following cycle conditions:
a reaction at 94° C. for 5 minutes was carried out; and
a cycle consisting of a reaction at 94° C. for 30 seconds, a reaction at 55° C. for 30 seconds, and a reaction at 72° C. for 1 minute and 30 seconds was repeated 25 times. The resulting PCR reaction products were purified using a High Pure PCR Product Purification Kit (manufactured by Roche) to confirm the mutations sites. After confirming that mutations corresponding to all amino acid substitutions for the 153rd amino acid were obtained, plasmids containing the mutated genes were purified using a QIAprep Spin Miniprep Kit (manufactured by QIAGEN).

These plasmids were introduced into the dnmV-disrupted strain described in Example 1 by conjugal transfer, and the amounts of epidaunorubicin produced by the resulting transformants were determined. As a result, it was confirmed that the productivity was improved by substitutions with amino acids other than proline, in comparison with the wild type.

TABLE 3

| | Amino acid | Amount of epidaunorubicin produced (relative ratio %) |
|---|---|---|
| 1 | Isoleucine | 175 |
| 2 | Valine | 136 |
| 3 | Phenylalanine | 124 |
| 4 | Leucine | 150 |
| 5 | Asparagine | 176 |
| 6 | Aspartic Acid | 132 |
| 7 | Histidine | 153 |
| 8 | Tyrosine | 107 |
| 9 | Threonine | 179 |
| 10 | Proline | 12 |
| 11 | Serine | 165 |
| 12 | Alanine | 152 |
| 13 | Cysteine | 153 |
| 14 | Arginine | 172 |
| 15 | Glycine | 162 |
| 16 | Glutamic Acid | 164 |
| 17 | Glutamine | 142 |
| 18 | Methionine | 154 |
| 19 | Tryptophan | 129 |
| 20 | Lysine (wild type) | 100 |

Example 3

Construction and Evaluation of Double Mutation of K153T and Q149S

Genomic DNA from the clone which was isolated in Example 1 and which had the highest productivity and the amino acid substitution of K153T was subjected to a PCR, using a combination of primer pSET153-R (SEQ ID NO: 3) and primer pSETermE-R (SEQ ID NO: 4), together with a PrimeSTAR HS DNA Polymerase (manufactured by Takara Bio Inc.), under the following cycle conditions:
a cycle consisting of a reaction at 98° C. for 10 seconds, a reaction at 60° C. for 5 seconds, and a reaction at 72° C. for 1 minute was repeated 25 times.

As a result, an amplified fragment of approximately 1 kbp was obtained. This amplified fragment was double-digested with BamHI and XbaI, and inserted between the BamHI and XbaI sites of plasmid pSET152-E* to obtain plasmid pEVA-E-1 containing evaE with the amino acid substitution of K153T. This plasmid pEVA-E-1 was subjected to a PCR, using a combination of primer pSET153-R (SEQ ID NO: 3) and primer Q149S-R (5'-TTCCGCTGTCAGCTTCTG-3', SEQ ID NO: 19), and a combination of primer Q149S-F (5'-TCGATCCTCAAGACGGCCACGGC-3', SEQ ID NO: 20) and primer pSETermE-R (SEQ ID NO: 4), together with a PrimeSTAR HS DNA Polymerase (manufactured by Takara Bio Inc.), under the same cycle conditions as above. The resulting PCR reaction products were purified using a High Pure PCR Product Purification Kit (manufactured by Roche) to obtain two DNA solutions. These two DNA solutions were phosphorylated with a T4 polynucleotide kinase (manufactured by Nippon Gene), and inserted between the BamHI and XbaI sites of plasmid pSET152-E* to obtain plasmid pEVA-E-2 containing evaE with the amino acid substitutions of K153T and Q149S (the 149th glutamine was substituted with serine).

This plasmid was introduced into the dnmV-disrupted strain described in Example 1 by conjugal transfer, and the amount of epidaunorubicin produced by the resulting transformant evaE-2 was determined in a similar fashion to that described in Example 1. As a result, it was confirmed that the productivity was improved in comparison with the strain before the mutation introduction.

TABLE 4

| Strain | Amount of epidaunorubicin produced (relative ratio %) |
|---|---|
| evaE/K153T | 100 |
| evaE-2 | 110 |

Example 4

Introduction of Random Mutations into K153T Mutant Gene

Plasmid pEVA-E-1 described in Example 3 was used as the template, using a GeneMorph II Random Mutagenesis Kit (manufactured by Stratagene) according to a manual attached thereto, to introduce random mutations into the K153T mutant gene.

The evaE fragments into which mutations were introduced were double-digested with BamHI and XbaI, and cloned between the BamHI and XbaI sites of plasmid pSET152-E* to prepare a genomic DNA library.

These plasmids obtained by the cloning were introduced into the dnmV-disrupted strain described in Example 1 by conjugal transfer, and the amounts of epidaunorubicin produced by the resulting transformants was determined in a similar fashion to that described in Example 1. As a result, it was found that a clone with a high productivity had an amino acid substitution of E306D (the 306th glutamic acid was substituted with aspartic acid) in addition to K153T, and the clone was designated evaE-3.

TABLE 5

| Strain | Amount of epidaunorubicin produced (relative ratio %) |
|---|---|
| evaE/K153T | 100 |
| evaE-3 | 110 |

Example 5

Construction and evaluation of triple mutants (K153T, C270R, and E306D) and quadruple mutants (Q42L, K153T, C270R, and E306D) of evaE Genomic DNA of evaE-3 isolated in Example 4 was subjected to a PCR, using a combination of primer pSET153-R (SEQ ID NO: 3) and primer T808C-R (5'-GTTCCA-CACGGGTCACCTCG-3', SEQ ID NO: 21), or a combination of primer T808C-F (5'-CGAGGTGACCCGTGTG-GAAC-3', SEQ ID NO: 22) and primer pSETermE-R (SEQ ID NO: 4), together with a PrimeSTAR HS DNA Polymerase (manufactured by Takara Bio Inc.), in a similar fashion to that described in Example 3. The resulting PCR reaction products were purified using a High Pure PCR Product Purification Kit (manufactured by Roche) to obtain two DNA solutions. These two DNA solutions were mixed, and a PCR was carried out, using this mixture as the template, a combination of primer pSET153-R (SEQ ID NO: 3) and primer pSETermE-R (SEQ ID NO: 4), and a PrimeSTAR HS DNA Polymerase (manufactured by Takara Bio Inc.), in a similar fashion to that described in Example 3. The amplified fragment was double-digested with BamHI and XbaI, and inserted between the BamHI and XbaI sites of plasmid pSET152-E* to obtain plasmid pEVA-E-4 containing evaE with the amino acid substitutions of K153T, C270R, and E306D.

Plasmid pEVA-E-4 was subjected to a PCR, using a combination of primer pSET153-R (SEQ ID NO: 3) and primer A125T-R (5'-ACGGTCGTCTCGGCTAGGCCGGGCG-3', SEQ ID NO: 23), or a combination of primer A125T-F (5'-GCCCGCGCCCGGCCTAGCCGAGACG-3', SEQ ID NO: 24) and primer pSETermE-R(SEQ ID NO: 4), together with a PrimeSTAR HS DNA Polymerase (manufactured by Takara Bio Inc.), in a similar fashion to that described in Example 3. The resulting PCR reaction products were purified using a High Pure PCR Product Purification Kit (manufactured by Roche) to obtain two DNA solutions. These two DNA solutions were mixed, and a PCR was carried out, using this mixture as the template, a combination of primer pSET153-R (SEQ ID NO: 3) and primer pSETermE-R (SEQ ID NO: 4), and a PrimeSTAR HS DNA Polymerase (manufactured by Takara Bio Inc.), in a similar fashion to that described in Example 3. The amplified fragment was double-digested with BamHI and XbaI, and inserted between the BamHI and XbaI sites of plasmid pSET152-E* to obtain plasmid pEVA-E-5 containing evaE with the amino acid substitutions of Q42L, K153T, C270R, and E306D.

This plasmid pEVA-E-5 was introduced into the dnmV-disrupted strain described in Example 1 by conjugal transfer, and the amount of epidaunorubicin produced by the resulting transformant evaE-5 was determined in a similar fashion to that described in Example 1. As a result, it was found that the productivity was improved in comparison with the strain before the mutation introduction.

TABLE 6

| Strain | Amount of epidaunorubicin produced (relative ratio %) |
|---|---|
| evaE/K153T | 100 |
| evaE-5 | 126 |

INDUSTRIAL APPLICABILITY

The ketoreductase mutant of the present invention can be used for the production of daunorubicin derivatives.

Although the present invention has been described with reference to specific embodiments, various changes and modifications obvious to those skilled in the art are possible without departing from the scope of the appended claims.

FREE TEXT IN SEQUENCE LISTING

Features of "Artificial Sequence" are described in the numeric identifier <223> in the Sequence Listing.

The nucleotide sequences of SEQ ID NOS: 2 to 24 are synthetic DNAs. The symbol "n" in SEQ ID NOS: 5 to 12 represents an arbitrary nucleotide.

The invention claimed is:

1. A ketoreductase mutant that differs from a non-mutant ketoreductase in amino acid sequence by 1-5 residues,
wherein the non-mutant ketoreductase comprises the amino acid sequence of SEQ ID NO: 1, or comprises a polypeptide having an amino acid sequence at least 90% identical to SEQ ID NO: 1,
wherein the differing 1-5 residues in said mutant are selected from the group consisting of the residues in said mutant that are located at positions which correspond to positions 42, 149, 153, 270 and 306 of SEQ ID NO: 1, and wherein the amino acids at said differing 1-5 residues in said mutant are different from the amino acids located at the corresponding positions in SEQ ID NO: 1.

2. The ketoreductase mutant according to claim 1, wherein the amino acid in said mutant located at the position corresponding to the 42nd amino acid in the amino acid sequence of SEQ ID NO: 1 is a leucine.

3. The ketoreductase mutant according to claim 1, wherein the amino acid in said mutant located at the position corresponding to the 149th amino acid in the amino acid sequence of SEQ ID NO: 1 is a serine.

4. The ketoreductase mutant according to claim 1, wherein the amino acid in said mutant located at the position corresponding to the 153rd amino acid in the amino acid sequence of SEQ ID NO: 1 is an amino acid other than proline.

5. The ketoreductase mutant according to claim 1, wherein the amino acid in said mutant located at the position corresponding to the 270th amino acid in the amino acid sequence of SEQ ID NO: 1 is an arginine.

6. The ketoreductase mutant according to claim 1, wherein the amino acid in said mutant located at the position corresponding to the 306th amino acid in the amino acid sequence of SEQ ID NO: 1 is an aspartic acid.

7. An isolated polynucleotide which encodes the ketoreductase mutant according to claim 1.

8. A transformant which is prepared by introducing the polynucleotide according to claim 7 into a host actinobacterium originally capable of producing daunomycin to impart an ability to produce a daunomycin derivative.

9. The transformant according to claim 8, wherein the host actinobacterium is *Streptomyces coeruleorubidus*.

10. A process of producing a daunomycin derivative, comprising the steps of: cultivating the transformant according to claim 9, and collecting the daunomycin derivative from the obtained culture broth.

* * * * *